(12) United States Patent
Funane et al.

(10) Patent No.: US 10,828,503 B2
(45) Date of Patent: Nov. 10, 2020

(54) ENERGY EMISSION DEVICE

(71) Applicant: HITACHI, LTD., Tokyo (JP)

(72) Inventors: Tsukasa Funane, Tokyo (JP); Hiroki Sato, Tokyo (JP)

(73) Assignee: HITACHI, LTD., Tokyo (JP)

( * ) Notice: Subject to any disclaimer, the term of this patent is extended or adjusted under 35 U.S.C. 154(b) by 401 days.

(21) Appl. No.: 15/761,115

(22) PCT Filed: May 12, 2016

(86) PCT No.: PCT/JP2016/064081
§ 371 (c)(1),
(2) Date: Mar. 19, 2018

(87) PCT Pub. No.: WO2017/195309
PCT Pub. Date: Nov. 16, 2017

(65) Prior Publication Data
US 2018/0256911 A1 Sep. 13, 2018

(51) Int. Cl.
*A61N 2/00* (2006.01)
*A61B 5/00* (2006.01)
(Continued)

(52) U.S. Cl.
CPC .......... *A61N 2/002* (2013.01); *A61B 5/14507* (2013.01); *A61B 5/407* (2013.01);
(Continued)

(58) Field of Classification Search
CPC .......... A61N 2/002; A61N 2/006; A61N 2/02; A61B 5/4809; A61B 5/4812
See application file for complete search history.

(56) References Cited

U.S. PATENT DOCUMENTS

2005/0020945 A1   1/2005  Tosaya et al.
2006/0161039 A1*  7/2006  Juliana ............... A61N 2/006
                                                          600/9
(Continued)

FOREIGN PATENT DOCUMENTS

JP   2005-296177 A   10/2005
JP   2010-504843 A    2/2010
(Continued)

OTHER PUBLICATIONS

International Search Report of PCT/JP2016/064081 dated Aug. 2, 2016.

*Primary Examiner* — Christine H Matthews
(74) *Attorney, Agent, or Firm* — Mattingly & Malur, PC

(57) ABSTRACT

The present invention provides an energy emission device comprising: one or a plurality of energy emitters for emitting at least one type of energy selected from the group consisting of an electromagnetic wave or an electromagnetic stimulation, an elastic wave, an oscillatory wave and heat to at least one position of a subject selected from the group consisting of the brain, the spinal cord, the cerebrospinal fluid or the flow passage thereof and the brain cell interstitial fluid or the flow passage thereof; an energy controller for controlling an amount of energy emitted from the energy emitters; and a sensor for obtaining information relating to wakefulness and/or a sleeping state of the subject, in which the energy controller controls the amount of energy emitted depending on the information relating to the wakefulness and/or the sleeping state.

19 Claims, 13 Drawing Sheets

(51) Int. Cl.

| | | |
|---|---|---|
| *A61H 23/00* | (2006.01) | |
| *A61B 5/145* | (2006.01) | |
| *A61H 23/02* | (2006.01) | |
| *A61F 7/00* | (2006.01) | |
| *A61N 2/02* | (2006.01) | |
| *A61N 7/00* | (2006.01) | |
| *A61N 5/06* | (2006.01) | |
| *A61B 5/01* | (2006.01) | |
| *A61B 5/0205* | (2006.01) | |
| *A61B 5/024* | (2006.01) | |
| *A61B 5/03* | (2006.01) | |
| *A61B 5/0476* | (2006.01) | |
| *A61B 5/107* | (2006.01) | |
| *A61B 5/11* | (2006.01) | |
| *A61N 5/067* | (2006.01) | |

(52) U.S. Cl.
CPC .......... *A61B 5/4064* (2013.01); *A61B 5/4809* (2013.01); *A61B 5/4812* (2013.01); *A61B 5/4836* (2013.01); *A61B 5/742* (2013.01); *A61F 7/00* (2013.01); *A61H 23/00* (2013.01); *A61H 23/02* (2013.01); *A61N 2/006* (2013.01); *A61N 2/02* (2013.01); *A61N 7/00* (2013.01); *A61B 5/0077* (2013.01); *A61B 5/01* (2013.01); *A61B 5/024* (2013.01); *A61B 5/02055* (2013.01); *A61B 5/031* (2013.01); *A61B 5/032* (2013.01); *A61B 5/0476* (2013.01); *A61B 5/1077* (2013.01); *A61B 5/11* (2013.01); *A61B 2560/0242* (2013.01); *A61F 2007/0024* (2013.01); *A61H 2201/0134* (2013.01); *A61H 2201/0149* (2013.01); *A61H 2201/1609* (2013.01); *A61H 2201/50* (2013.01); *A61N 5/06* (2013.01); *A61N 2005/067* (2013.01); *A61N 2005/0651* (2013.01); *A61N 2007/0026* (2013.01); *A61N 2007/0039* (2013.01); *A61N 2007/0091* (2013.01)

(56) References Cited

U.S. PATENT DOCUMENTS

| | | |
|---|---|---|
| 2008/0081941 A1 | 4/2008 | Tononi |
| 2009/0187062 A1 | 7/2009 | Saitoh |
| 2010/0256438 A1 | 10/2010 | Mishelevich et al. |
| 2014/0058189 A1* | 2/2014 | Stubbeman ............ A61N 2/006 600/13 |

FOREIGN PATENT DOCUMENTS

| | | |
|---|---|---|
| JP | 2010-536496 A | 12/2010 |
| JP | 2013-059683 A | 4/2013 |

\* cited by examiner

ENERGY EMISSION DEVICE

TECHNICAL FIELD

The present invention relates to an energy emission device and a method for controlling flow rates of the cerebrospinal fluid and/or the brain cell interstitial fluid by emitting energy such as electromagnetic wave, oscillation, ultrasound (acoustic) to an interior of a living body.

BACKGROUND ART

Alzheimer's disease which is one of neurodegenerative diseases is said to account for a highest percentage, exceeding approximately 60%, among causative diseases of dementia. Examples of symptoms of Alzheimer's disease include memory impairment, impaired linguistic ability or judgment, problematic behavior such as wandering, depressive symptoms, consciousness muddle, hallucinations, illusion, and delusion.

However, no fundamental treatment for Alzheimer's disease has been established yet and the problem is that there is no choice but to depend on symptomatic treatment and symptomatic improvement therapy. On the other hand, proportion of elderly people is estimated to continue to increase in the future and the importance of early stage diagnosis and early stage treatment of Alzheimer's disease is estimated to grow significantly.

A main pathological feature of the brain of a patient of Alzheimer's disease is that deposition of amyloid beta (Aβ) protein (or Aβ peptide) and neurofibrillary tangle occur in the limbic system of the brain (hippocampus, amygdala) and in other cortical and subcortical regions. Examples of causes of Alzheimer's disease include a theory that assumes a reduction of acetylcholine as a cause (acetylcholine hypothesis) and a theory that assumes an abnormal increase of Aβ as a trigger of Alzheimer's disease (amyloid cascade hypothesis). Diagnostic methods using various amyloid imaging techniques on a basis of the amyloid cascade hypothesis are under development. A reduction of Aβ clearance due to cleavage by an amyloid precursor protein (APP)-specific enzyme or imbalance between Aβ production and discharge is believed to be one factor for accumulation of Aβ. In familiar Alzheimer-type dementia, various risk genes (APP genes, presenilin genes (two kinds)) or protein (apolipoprotein) are considered to be associated with an onset of the disease.

As described above, although accumulation, outside brain cells, of amyloid beta (Aβ) protein produced in the brain cells is believed to be one of causes of Alzheimer's disease, it is difficult to prevent accumulation and deposition of Aβ and further remove accumulated Aβ.

Patent Literature 1 discloses emission of ultrasound to a cerebrospinal fluid (CSF) and the brain or the spinal cord region, and emission by a plurality of emitters with a time difference/phase difference for the treatment of neurodegenerative diseases.

CITATION LIST

Patent Literature

Patent Literature 1: US Patent Application Publication No. 2005/0020945

SUMMARY OF INVENTION

Technical Problem

It is an object of the present invention to provide a means and a method for promoting discharge of intracerebral waste such as Aβ protein and unnecessary intracerebral substances by controlling flow rates of the cerebrospinal fluid and/or the brain cell interstitial fluid and promoting convection.

Solution to Problem

As a result of intensive studies to solve the above-described problems, the present inventor has found that efficiently promoting exchange between a cerebrospinal fluid (CSF) and a brain cell interstitial fluid (ISF) (CSF-ISF exchange) through emission of energy (light, oscillation, acoustic or the like) during sleep so as not to interfere with sleep onset and sleep re-onset will be able to efficiently promote discharge of intracerebral waste such as Aβ protein and unnecessary intracerebral substances.

That is, an energy emission device according to the present invention comprises a means for efficiently emitting energy during sleep to control flow rates of the cerebrospinal fluid and/or the brain cell interstitial fluid and promote discharge of waste or the like. In order to efficiently promote discharge of waste such as Aβ, the device monitors information relating to wakefulness or a sleeping state of a subject and emits energy (light, oscillation, acoustic) to the cerebrospinal fluid and/or the brain cell interstitial fluid according to the information. Moreover, the device performs control depending on a sleep depth or a sleeping level so that a body temperature does not rise exceeding a predetermined value. For example, the device is configured so as to emit energy only in a non-REM (non rapid eye movement: non-REM) sleeping stage 4 (during this time, the body temperature is believed to be low). In order to efficiently generate (heat) convection or to prevent interference with sleep onset, the device emits energy to the cerebrospinal fluid and/or the brain cell interstitial fluid at different positions and in temporally different intensity patterns.

Advantageous Effects of Invention

According to the present invention, by emitting energy in accordance with the sleep depth during sleep in which waste discharge has a highest efficiency, it is possible to deliver energy to the cerebrospinal fluid and/or the brain cell interstitial fluid without interfering with the sleep and while saving consumed energy. Furthermore, emitting energy in accordance with the sleep depth or emitting energy while monitoring the body temperature, deep body temperature or skin temperature provides an effect of avoiding interference with a comfortable sleep. Furthermore, emitting energy in accordance with a CSF flow passage allows an effect of being able to efficiently promote the CSF flow to be expected. Promoting the CSF flow in this way provides an effect of eliminating (preventing) blocking of the CSF flow and is effective in prevention and treatment of Alzheimer's disease and other diseases.

DESCRIPTION OF EMBODIMENTS

Figure 1:
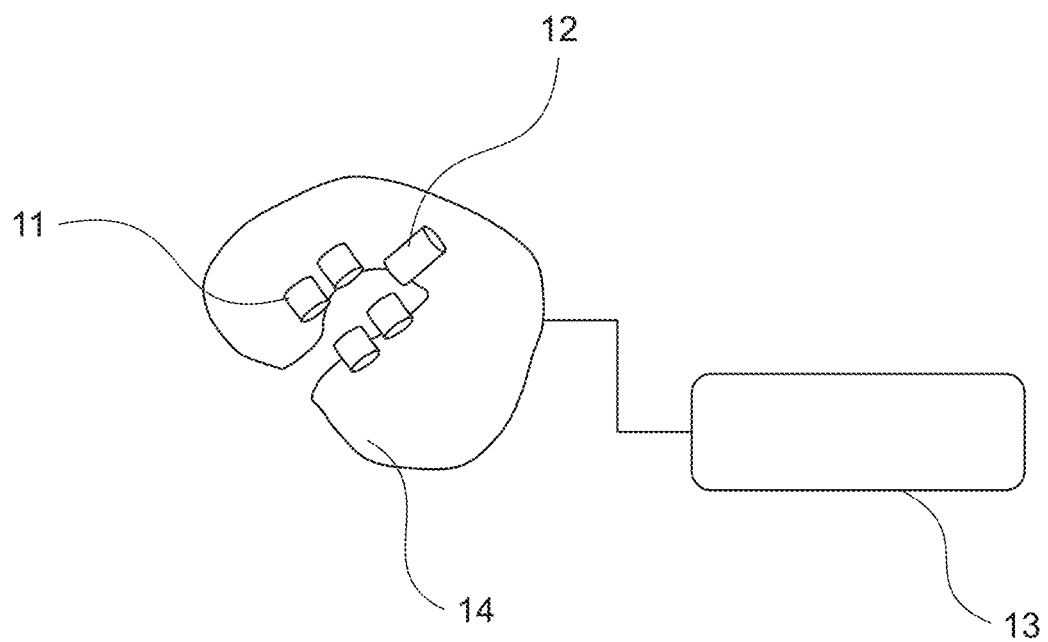
FIG. 1 shows a conceptual diagram of a neck pillow type energy emission device.

The present invention relates to a device and a method for emitting energy so as to control a flow rate(s) of the cerebrospinal fluid (CSF) and/or the brain cell interstitial fluid (ISF). The cerebrospinal fluid (CSF) plays an important role in discharging Aβ protein and intracerebral waste and it is also reported that solutes such as Aβ existing outside brain cells are discharged through exchange with the brain cell interstitial fluid (ISF) via a perivascular route, and furthermore it is revealed that the CSF-ISF exchange is promoted during sleep (Iliff, J. J. et al., Sci Transl Med, 2012, 4(147):147ra111; Xie, L. et al., Science, 2013, 342(6156): 373-7).

Thus, according to the present invention, information relating to wakefulness and/or a sleeping state of a subject is obtained and an amount of energy emitted to the subject is controlled depending on the information relating to the wakefulness and/or sleeping state. It is thereby possible to efficiently perform CSF-ISF exchange during sleep of the subject and prevent interference with sleep onset and sleep re-onset.

According to an aspect, the energy emission device of the present invention comprises:

one or a plurality of energy emission means for emitting at least one type of energy selected from the group consisting of an electromagnetic wave or an electromagnetic stimulation, an elastic wave, an oscillatory wave and heat to at least one position of a subject selected from the group consisting of the brain, the spinal cord, the cerebrospinal fluid or the flow passage thereof and the brain cell interstitial fluid or the flow passage thereof;

an energy controlling means for controlling an amount of energy emitted from the energy emission means; and a means for obtaining information relating to wakefulness and/or a sleeping state of the subject, in which the energy controlling means controls the amount of energy emission depending on the information relating to the wakefulness and/or the sleeping state.

The energy emission means is not particularly limited if it can emit at least one type of energy selected from the group consisting of an electromagnetic wave (e.g., light) or an electromagnetic stimulation (e.g., magnetic field), an elastic wave, an oscillatory wave (e.g., ultrasound) and heat. Examples thereof may include a light source such as a laser diode (LD) and a light-emitting diode (LED), a piezoelectric transducer, ultrasound emission means such as an ultrasound resonator. The energy controlling means is not particularly limited either if it can control energy emission timing and emission intensity or the like of the energy emission means, and can be selected as appropriate so as to suit the energy emission means used.

The subject is not particularly limited if it is an animal, a flow rate(s) of the cerebrospinal fluid and/or the brain cell interstitial fluid of which can be controlled and from which promotion of discharge of intracerebral waste can be expected. Examples of the subject include humans, nonhuman primates (monkey, gorilla, chimpanzee, baboon or the like), pet animals (dog, cat or the like), and domestic animals (cow, horse, sheep or the like) but humans are preferably selected as the subjects.

The position(s) of energy emission to the subject needs to be a position(s) where it is possible to control a flow rate(s) of the cerebrospinal fluid and/or the brain cell interstitial fluid and promote convection of the cerebrospinal fluid (CSF). Such position(s) can be at least one position selected from the group consisting of the brain, the spinal cord, the cerebrospinal fluid or the flow passage thereof and the brain cell interstitial fluid or the flow passage thereof.

Figure 4:
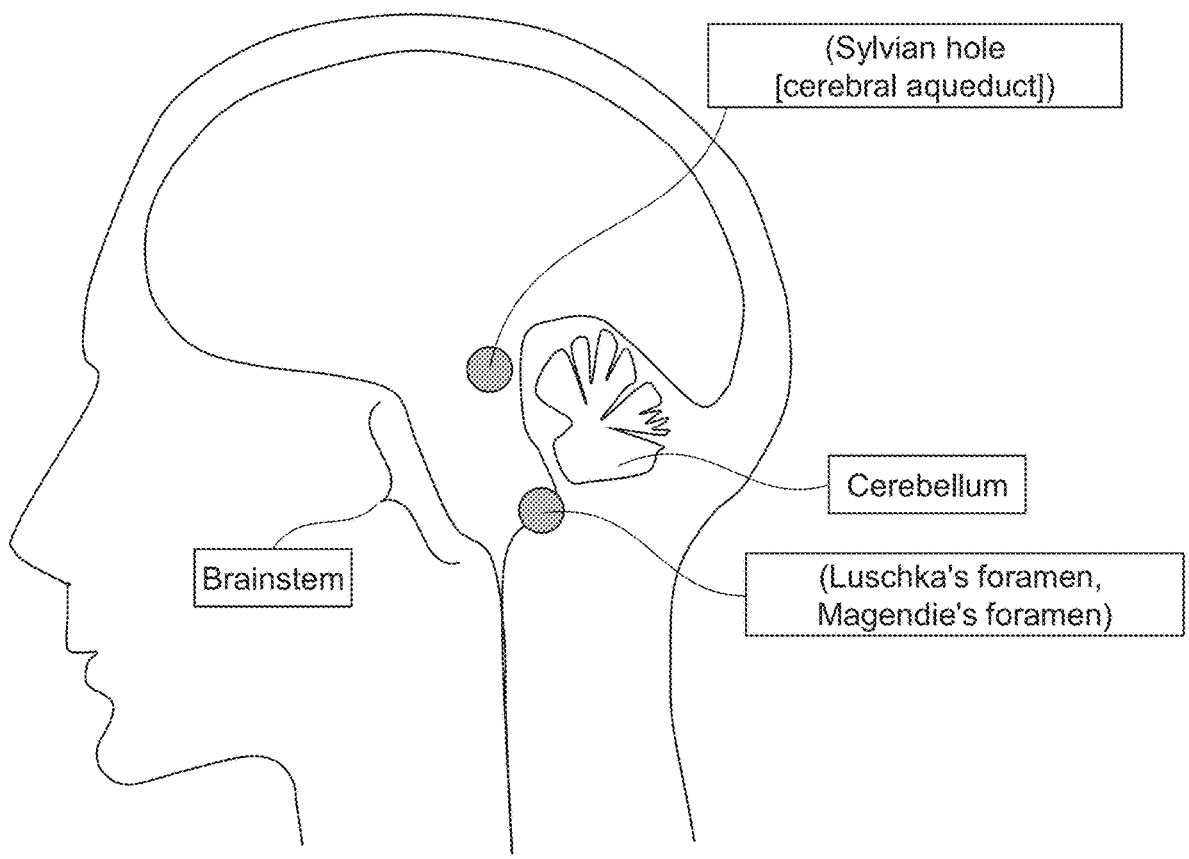
FIG. 4 shows a diagram illustrating an example of an emission target position in a cerebrospinal fluid flow passage.

FIG. 4 illustrates specific examples of emission target positions in the cerebrospinal fluid flow passage. As the emission points, for example, a Sylvian fissure (cerebral aqueduct) which is a passage in proximity to the brainstem from the fourth cerebral ventricle to the subarachnoid cavity, Luschka's foramen (left/right outside holes of fourth cerebral ventricle) and Magendie's foramen (median hole of fourth cerebral ventricle) can be set. Energy may be preferably selectively emitted to these cerebrospinal fluid flow passages so as to have a maximum energy distribution. This provides an effect of being able to efficiently prevent clogging of the cerebrospinal fluid in these holes and promote discharge of the cerebrospinal fluid. Furthermore, for example, emission point(s) may be set to the front side of the cerebellum or the vicinity of the bottom end thereof. Furthermore, by causing the temperature in the vicinity of the above-described holes to rise, it is possible to induce convection of the cerebrospinal fluid in an arbitrary direction due to temperature and pressure gradients in the flow passage. Since energy emitted from the outside is generally an energy supply which is unnecessary for normal brain tissues, energy emission can be preferably performed while avoiding peripheral brain tissues such as the cerebellum, the brainstem (diencephalon, mesencephalon, pons, and medulla oblongata). For that purpose, the energy emission device of the present invention may further comprise an emission position setting means for setting the emission position(s) of energy emitted from the energy emission means to the above-described position(s).

The wakefulness of the subject refers to a level of consciousness and is associated with a sleep level in the present specification. In human sleep, REM sleep and non-REM sleep are repeated and the non-REM sleep is known to vary from stage 1 to 4 depending on the depth thereof. The wakefulness or the sleep level can be determined by measuring a brain wave, a cardiac rate or the like. Furthermore, the information relating to the sleeping state refers to information on factors affecting the sleep level such as ambient brightness, hours (morning, evening or the like). According to the present invention, since more favorable effects can be achieved through energy emission during sleep, it is important that the energy controlling means should control the amount of energy emitted depending on information on the wakefulness of the subject or surroundings of the subject and/or control the start and end of emission.

Means for obtaining such information relating to wakefulness and/or a sleeping state is not limited, but the means can be, for example, a brain waves sensor, an acceleration (motion) sensor, an image sensor, an optical sensor and a heartbeat sensor.

The energy emission device according to the present invention controls a flow rate(s) of the cerebrospinal fluid and/or the brain cell interstitial fluid and controls energy emission with the amount of emission and time with which it is possible to promote convection of the cerebrospinal fluid (CSF). The amount of energy emission may vary depending on the energy emission means used and the age of the subject or the like, but energy may be emitted so as to ensure that energy of, for example, 400 to 800 J, preferably 600 J can be delivered to the target position(s). Although more energy is actually required because there are influences of heat emission, the amount of energy emission may be a value calculated as an amount of energy necessary for a temperature rise on the order of 0.5 degrees assuming that the amount of cerebrospinal fluid of an adult is 130 ml, the amount of production per day is 500 ml and the emission time is 8 hours. Furthermore, the energy emission time may also differ depending on the energy emission means used or the age of the subject or the like, but energy can be emitted, for example, during sleep (1 to 12 hours or the like), during non-REM sleep (approximately 30 minutes to approximately 2 hours). The frequency with which energy emission is performed may be set as appropriate such as once to 10 times a day, once every two days, once every three days, once a week or once a month.

The energy emission device according to the present invention may further comprise a structure information acquiring means for acquiring structure information of a shape of the head or a bony framework or the spinal cord of the subject and it is thereby possible to efficiently emit energy to the target position(s) of the subject.

The energy emission device according to the present invention may further comprise a temperature measuring means for measuring a temperature of the surface and/or the interior of the subject. Examples of such temperature measuring means include a clinical thermometer and a skin thermometer. Since the body temperature generally decreases during sleep (e.g., on the order of 0.5 degrees), and the body temperature decreases (e.g., on the order of 0.5 degrees) as the sleep level (REM sleep to non-REM sleep [stage 1 to 4]) deepens, it is possible to perform control so as to emit energy during sleep, preferably during non-REM sleep or more preferably during non-REM sleep at stage 3 or 4 by monitoring the body temperature using the temperature measuring means. Furthermore, since it is considered to be preferable to lower the body temperature for comfortable sleep, it is possible to control energy emission such that the body temperature does not rise in excess of a predetermined temperature (e.g., 0.5 degrees) through energy emission.

The energy emission device according to the present invention may further comprise a data storage section that stores various measured data and data to be used as a reference when setting energy emission, an analysis section that analyzes the data, and a display section for displaying the data and information relating to energy emission (amount of energy emission, emission sequence) or the like.

Furthermore, the present invention provides an energy emission method. The energy emission method according to the present invention comprises steps of obtaining information relating to wakefulness and/or a sleeping state of a subject, and emitting energy to at least one position selected from the group consisting of the brain, the spinal cord, the cerebrospinal fluid or the flow passage thereof and the brain cell interstitial fluid or the flow passage thereof of the subject, wherein the amount of energy emission is controlled depending on obtained information relating to the wakefulness and/or sleeping state. The energy to be emitted may be at least one type of energy selected from the group consisting of an electromagnetic wave or an electromagnetic stimulation, an elastic wave, an oscillatory wave and heat in the same way as described above. In the energy emission method according to the present invention, it may be determined whether or not to perform the step of emitting energy depending on the obtained information relating to wakefulness and/or a sleeping state.

Hereinafter, specific embodiments of the present invention will be described with reference to the accompanying drawings. Configuration blocks or components denoted by the same reference numerals among different drawings represent the same configuration blocks or components.

Example 1

FIG. 1 shows a conceptual diagram illustrating a neck pillow type energy emission device. The energy emission device is supposed to be worn around the neck of a subject. A cushion part 14 is made of an elastic material and an energy emission section 11 is attached to the skin around the neck of the subject. The energy emission section 11 may be an energy emission means set in contact with or nearly in contact with, for example, the skin of the subject such as a light source, for example, a laser diode (LD), a light-emitting diode (LED) or a piezoelectric transducer or an ultrasonic transducer. The energy emission device further comprises an energy control section 13 for controlling energy emission timing or emission intensity. The energy control section 13 controls energy emission timing or emission intensity depending on a sleeping state detected by a sleeping state detection section 12. Such a configuration allows energy emission to be efficiently performed during sleep without placing any burden on the subject. Furthermore, since a small-sized and simple device configuration is adopted, the energy emission device can be used at home while getting medical treatment at home.

The device having such a configuration provides a means for promoting CSF discharge during sleep and CSF-ISF exchange via a perivascular space through energy emission along a flow passages of the cerebrospinal fluid (CSF) and the brain cell interstitial fluid (ISF) of the subject according to information on wakefulness, a sleep level, a respiration state, ambient brightness (acquired using an acceleration sensor, a motion sensor, a respiration sensor, a heartbeat sensor, an optical sensor or the like). The device promotes effective CSF and/or ISF convection in vivo by temporally changing an emission mode, emission timing or emission intensity depending on the location.

The body temperature is generally known to decrease during sleep (e.g., on the order of 0.5 degrees). Furthermore, it is considered to be preferable that the body temperature be lowered for comfortable sleep. However, since the body temperature is on the rise when energy is emitted, to solve this problem, the emission level may be controlled by providing a skin thermometer or a perspiration meter and watching the reading so that the temperature rise or the perspiration level falls within a predetermined range.

Since the body temperature decreases (on the order of 0.5 degrees) as the sleep level (REM sleep to non-REM sleep [stage 1 to 4]) deepens, energy emission may be controlled so as not to interfere with comfortable sleep and such that the body temperature does not rise by a predetermined temperature (e.g., 0.5 degrees) (within 0.5 degrees, the body temperature never exceeds the body temperature before sleep). Note that the wakefulness and the sleep level may be estimated using a microwave radar, a displacement sensor, a CCD or CMOS image sensor or the like.

Example 2

Figure 2:
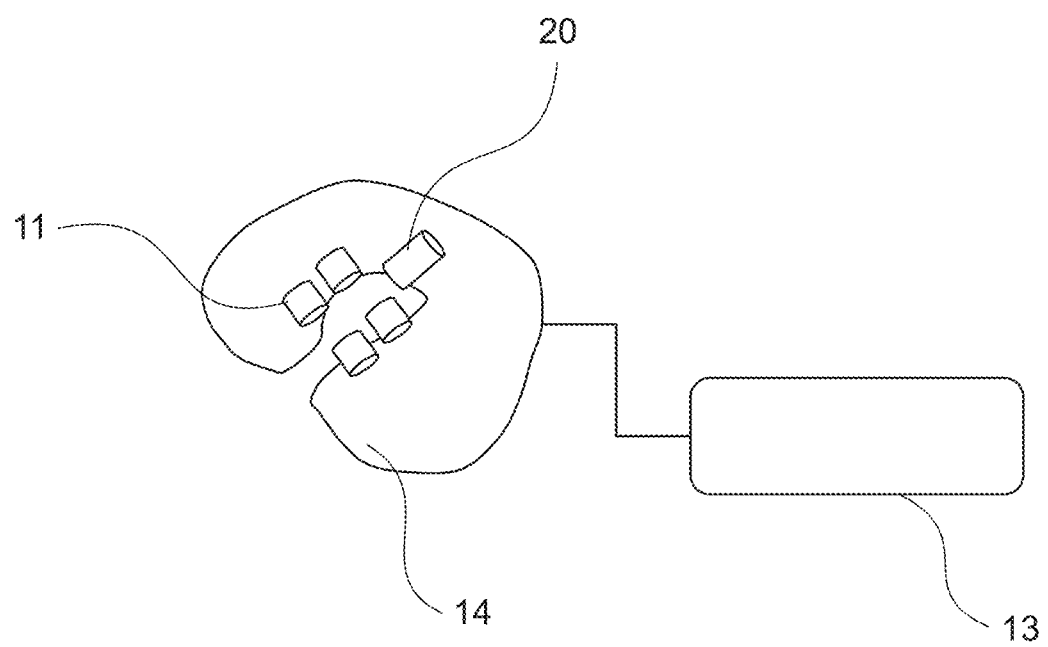
FIG. 2 shows a conceptual diagram of the neck pillow type energy emission device that controls emission energy depending on ambient light environments detected by an optical sensor.

FIG. 2 shows a conceptual diagram of a neck pillow type energy emission device that controls emission energy depending on ambient light environments detected by an optical sensor. The energy emission section 11 and the cushion part 14 are arranged for purposes similar to those of Example 1 (FIG. 1). An optical sensor 20 is configured to measure ambient light environments and the energy control section 13 is configured to operate only when the ambient light intensity acquired by the optical sensor 20 is lower than a predetermined value or to automatically start operating when the ambient light intensity is smaller than a predetermined value. When the device of the present invention is used, the subject is instructed that the subject is placed, for example, in a dark environment. In such a case, the optical sensor 20 plays a role as an ON/OFF switch of the device of the present invention. When there is bright ambient, if it is not the right time for energy emission according to the setting, emission is never started erroneously in that case, and so the device also functions as a safety device.

Example 3

Figure 3:
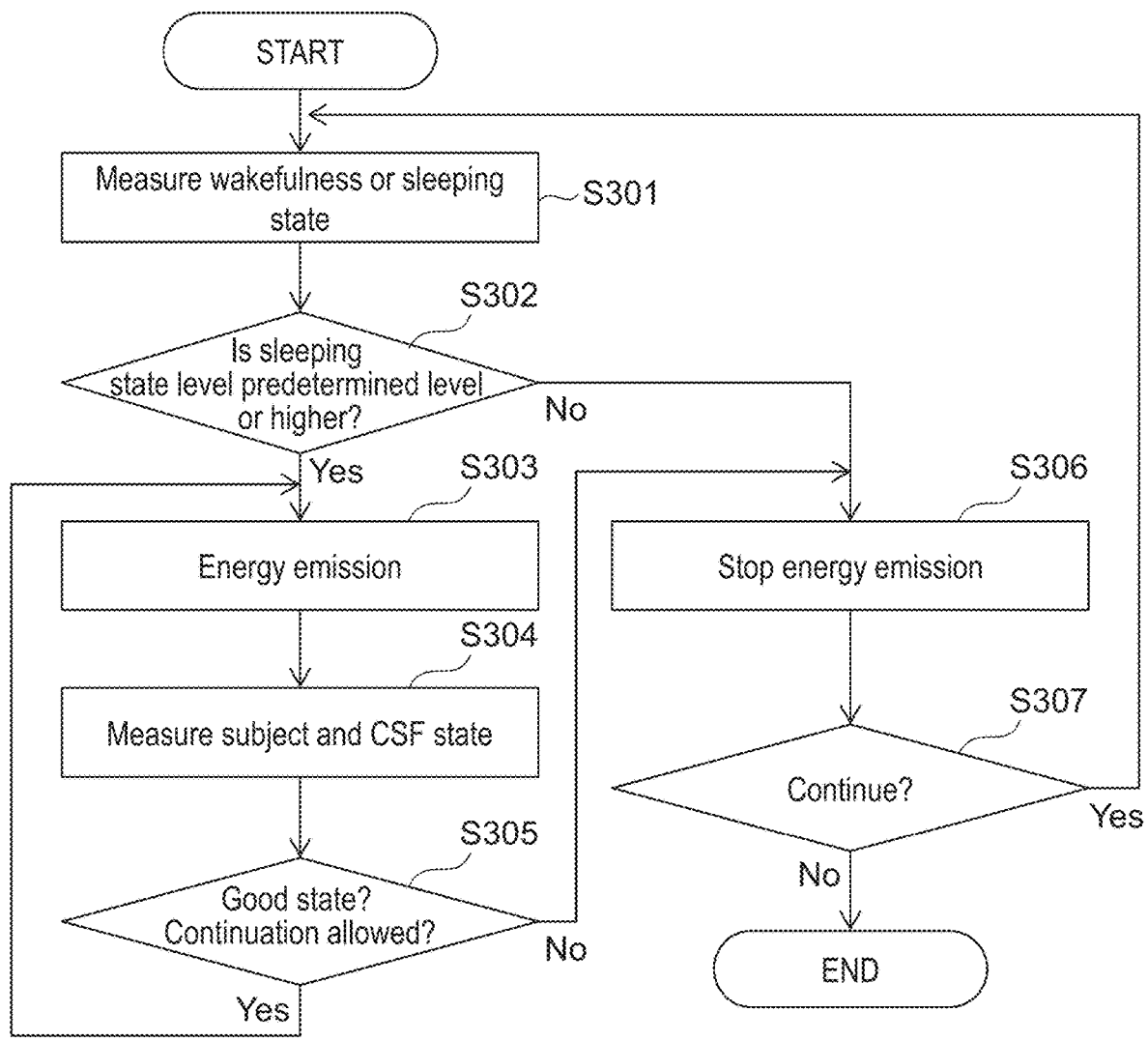
FIG. 3 is a flowchart showing how energy is emitted by monitoring wakefulness or a sleeping state of a subject, a state of the subject and a state of a cerebrospinal fluid (CSF).

FIG. 3 is a flowchart showing emission of energy while monitoring wakefulness or a sleeping state of the subject, a state of the subject and a state of the cerebrospinal fluid (CSF). After a start, wakefulness or a sleeping state of the subject is measured (step S301). It is determined whether the sleeping state level is equal to or higher than a predetermined value or whether the wakefulness level is equal to or lower than a predetermined value (step S302). It is determined whether the non-REM sleep is in stage 3 or 4 (deepest level). When "Yes" in step S302, energy emission is started (step S303). The states of the subject and the cerebrospinal fluid (CSF) are measured (step S304). For example, it may be determined whether a body temperature measured by a body thermometer, a skin temperature measured by a skin thermometer, a perspiration state measured by a perspiration meter or a cerebrospinal fluid flow measured by a cerebrospinal fluid flow monitor falls within a predetermined range or not and it may be determined whether the state is good or not and whether energy emission can be continued or not (step S305). For the body temperature, an initial temperature plus 0.5 degrees can be set as a threshold. In the determination in this step, a predetermined elapsed time or the like may be set to determine whether energy emission can be continued or not based on the elapsed time. When "Yes" in step S305, the flow moves to step S303. When "No" in step S302 or step S305, energy emission is stopped (step S306). It is then determined whether emission is to be continued or not (step S307). When "No" in step S307, the present flow is ended and when "Yes," the flow moves to step S301 and the present flow continues.

When there is no additional sensor such as a skin thermometer or perspiration meter, emitting energy only when the sleep level is deepest (non-REM sleep stage 4) is considered to be most efficient from the standpoint of waste discharge. In non-REM sleep stage 4, the body temperature is normally low and the body temperature is most unlikely to rise beyond the temperature before sleep onset despite energy emission, providing an effect of less affecting perspiration and hardly interfering with comfortable sleep.

Note that micro-streaming action using ultrasound to control shrinking of bubbles in a living body, a technology of ultrasonic cavitation or a heater may be used as the energy emission means. When using a heater, it is necessary to use a temperature monitor to control a body surface temperature or temperature inside the body so as not to exceed a predetermined temperature (e.g., 40° C.) from the standpoint of securing safety.

Example 4

Figure 5:
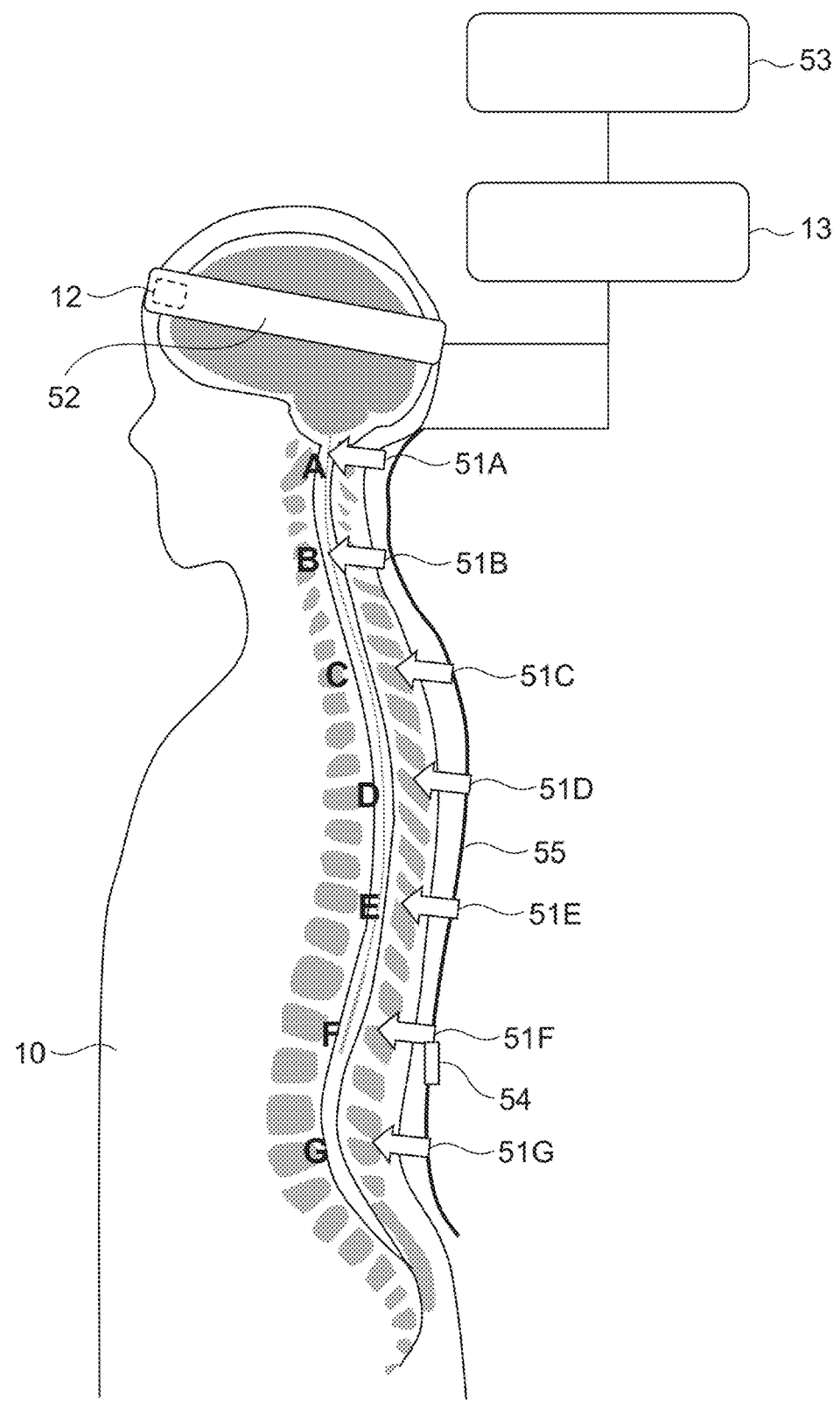
FIG. 5 is a diagram illustrating an example of the energy emission device disposed along the spine (vertebra).

FIG. 5 shows an example of an energy emission device disposed along the spine (vertebra). The device may also be set up on a bedding device such as a bed or a chair such as massage chair.

Emitters A (51A) to G (51G) are arranged on the subject 10 for emission at emission positions A to G respectively. The energy control section 13 controls emission timings and emission intensities of the emitters A (51A) to G (51G) using information of the sleeping state detection section 12, a skin temperature and body temperature monitor 52. A setup position, emission timing and emission intensity of each emitter may be displayed on a display section 53. Furthermore, a temperature measured by the skin temperature and body temperature monitor 52 may be displayed on the display section 53. In this way, CSF convection in the subject 10 can be optimized by making emission timing and emission intensity variable depending on a position at which emission is performed. That is, when a plurality of energy emitters are used, the plurality of energy emitters 51A to 51G are set up so as to be able to emit energy to a plurality of positions and the energy control section 13 changes emission timing and/or emission intensity depending on the positions. Furthermore, a cerebrospinal fluid monitoring means 54 may be an optical acoustic spectroscopic device, a near-infrared spectroscopic device, a light coherence tomography device, a fluorescence spectroscopic device, a magnetic resonance imaging method, a non-linear optical microscope or the like and the cerebrospinal fluid monitoring means 54 is a means for monitoring an amount of the cerebrospinal fluid or an in-vivo substance relating to the cerebrospinal fluid. The cerebrospinal fluid monitoring means 54 may be disposed along, for example, the spine (vertebra) and used to monitor effects of energy emission for measuring a flow rate of the cerebrospinal fluid or concentrations of substances in the cerebrospinal fluid.

Figure 6:
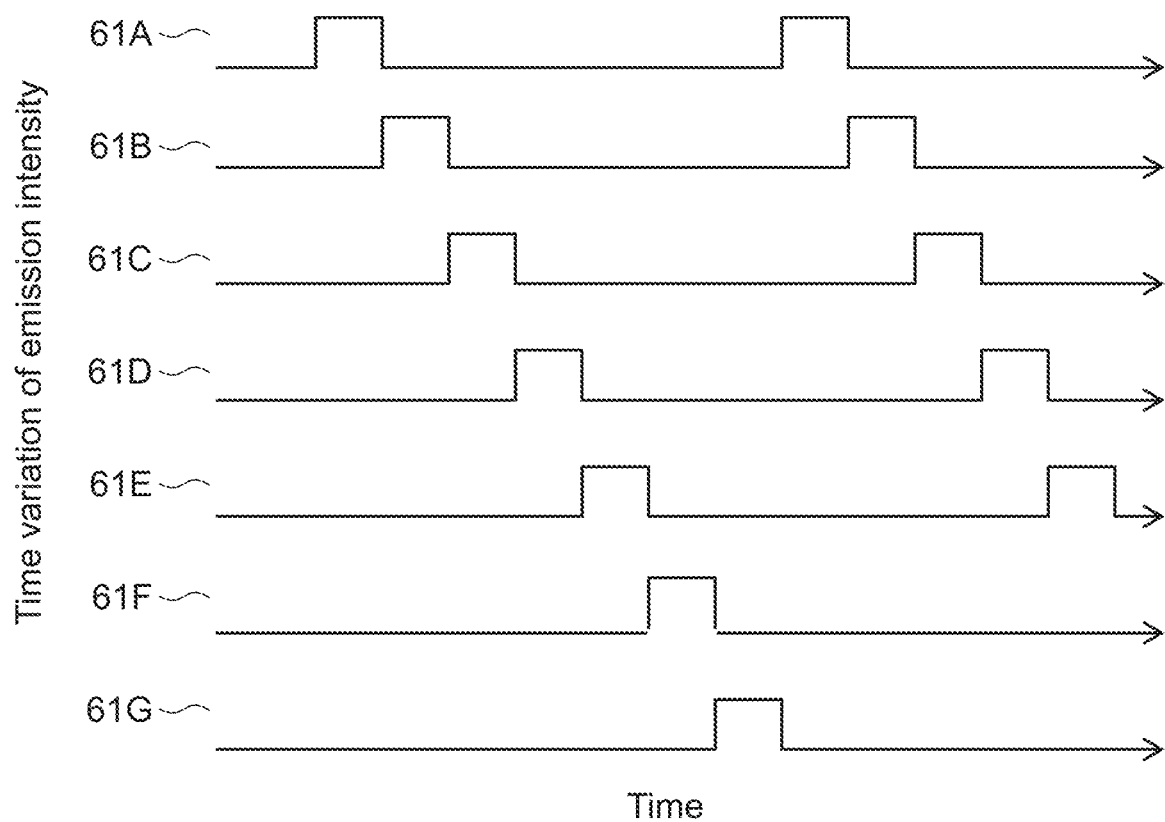
FIG. 6 is a graph illustrating an example of a time variation of emission intensity at positions A to G of a subject 10.

FIG. 6 illustrates an example of a time variation of emission intensity at the positions A to G of the subject 10. Reference numerals 61A to 61G denote time variations of intensities of energy emitted from the emitters 51A to 51G respectively. As shown in FIG. 6, the emission positions may be temporally scanned. At this time, by performing scanning in accordance with thermal expansion or transmission speed of an acoustic wave in the flow passage, the emitters may be configured so as not to interfere with energy waves generated through emission and further emphasize (multiply) the energy waves. In this way, by changing emission positions of energy (magnetic field or ultrasound or light), it is possible to provide effects of shifting timings at which energy is received according to locations of the CSF flow passages, effectively generating (heat) convection and controlling the convection.

Figure 7:
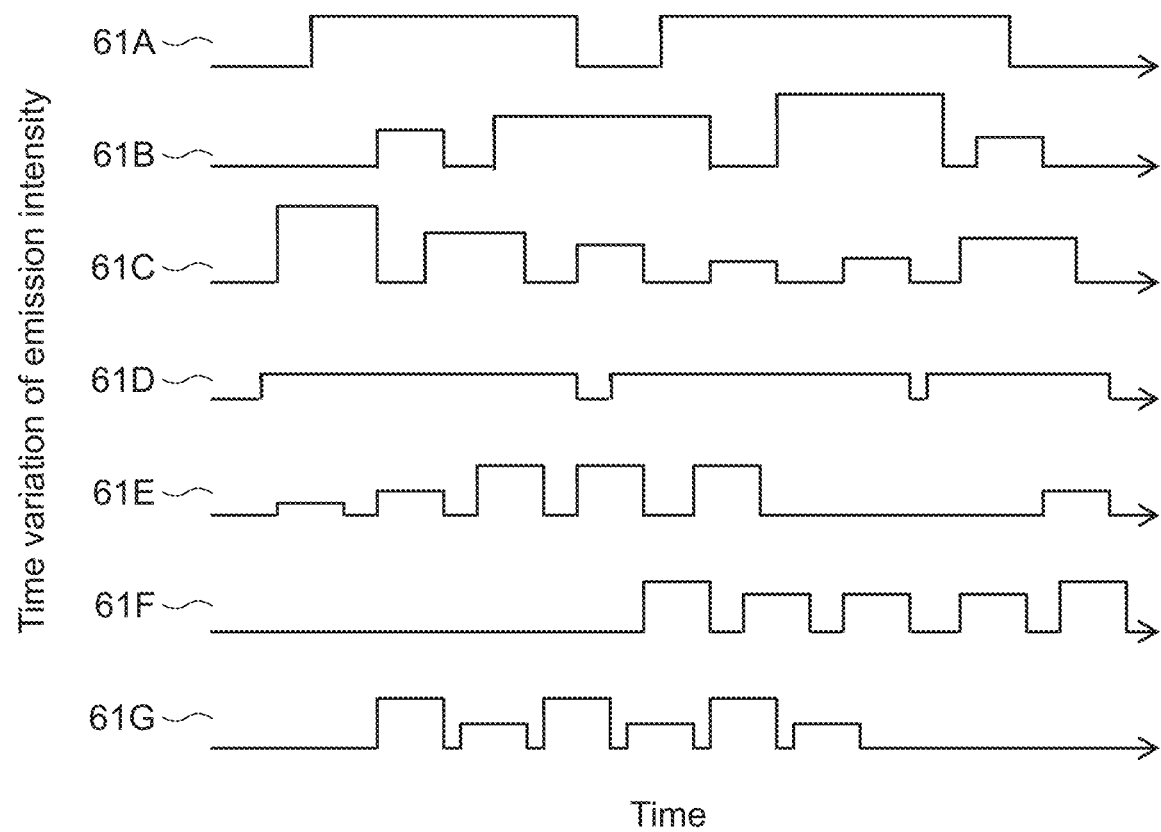
FIG. 7 is a graph illustrating an example of emission energy intensity patterns at positions A to G when energy having intensity shown by an arbitrary waveform is emitted.

FIG. 7 illustrates emission energy intensity patterns at the positions A to G when energy with intensities represented by arbitrary waveforms is emitted.

Energy need not be sequentially emitted depending on the locations, but the respective emitters can perform emission in their respective emission intensity patterns. These patterns may be inputted in advance or may be optimized while monitoring the patterns using the cerebrospinal fluid monitoring means 54 (FIG. 5). Furthermore, energy emission intensities are set depending on the positions so that light does not reach the retina of the subject in the case of light energy or so that oscillation does not reach the external ear or the internal ear in the case of sound wave energy. For this purpose, an energy detection means may be disposed in the vicinity of the retina, the external ear or the internal ear. This has an effect of keeping a sleep state without interfering with the sleep onset. By controlling emission intensities depending on the emission position and/or wakefulness in the above-described configuration, it is possible to shift the energy pattern received according to the location of the CSF flow passage, generate and control (heat) convection in the CSF flow passage.

Figure 8:
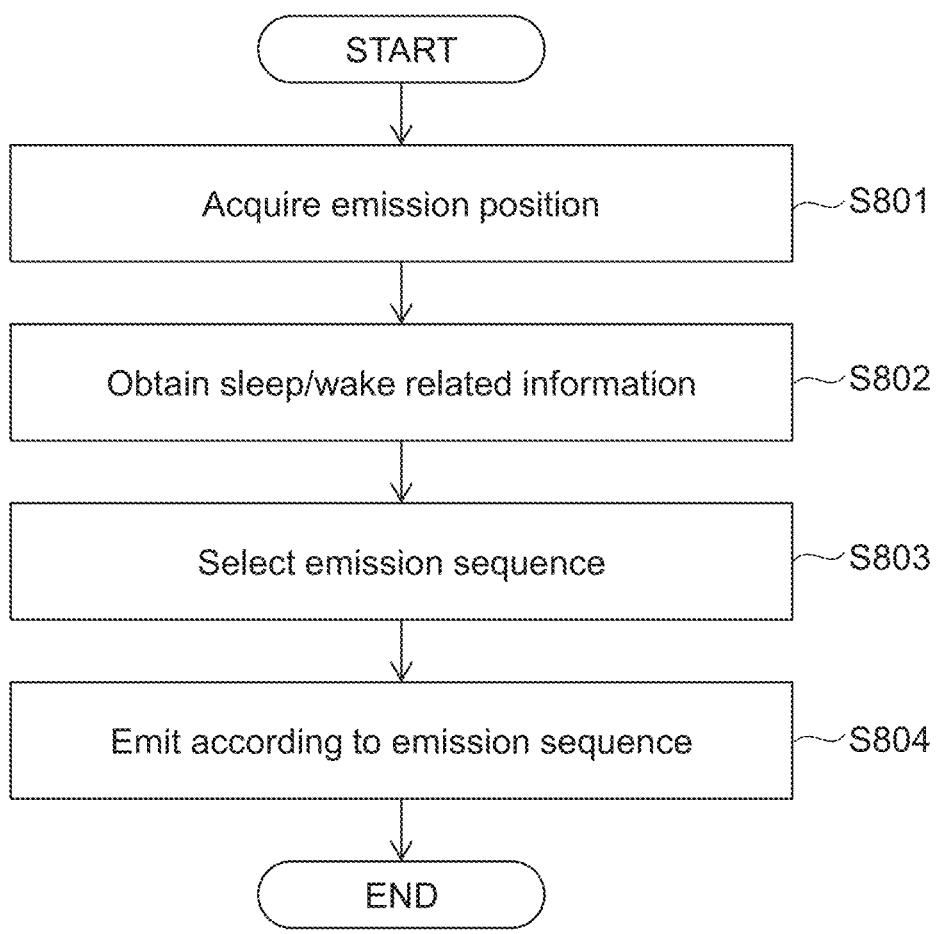
FIG. 8 is a flowchart showing how emission timing and/or emission intensity is changed depending on an emission position.

FIG. 8 is a flowchart showing how emission timing and/or emission intensity is changed depending on an emission position. In the present flow, energy emission positions are acquired first (step S801). Next, sleep/wake-related information (sleep level, wakefulness, surrounding information or the like) is obtained (step S802). Next, an emission sequence is selected (step S803). Finally, emission is performed according to the emission sequence (step S804). The CSF convection can be optimized by changing emission timing and emission intensity depending on the location.

Example 5

Figure 9:
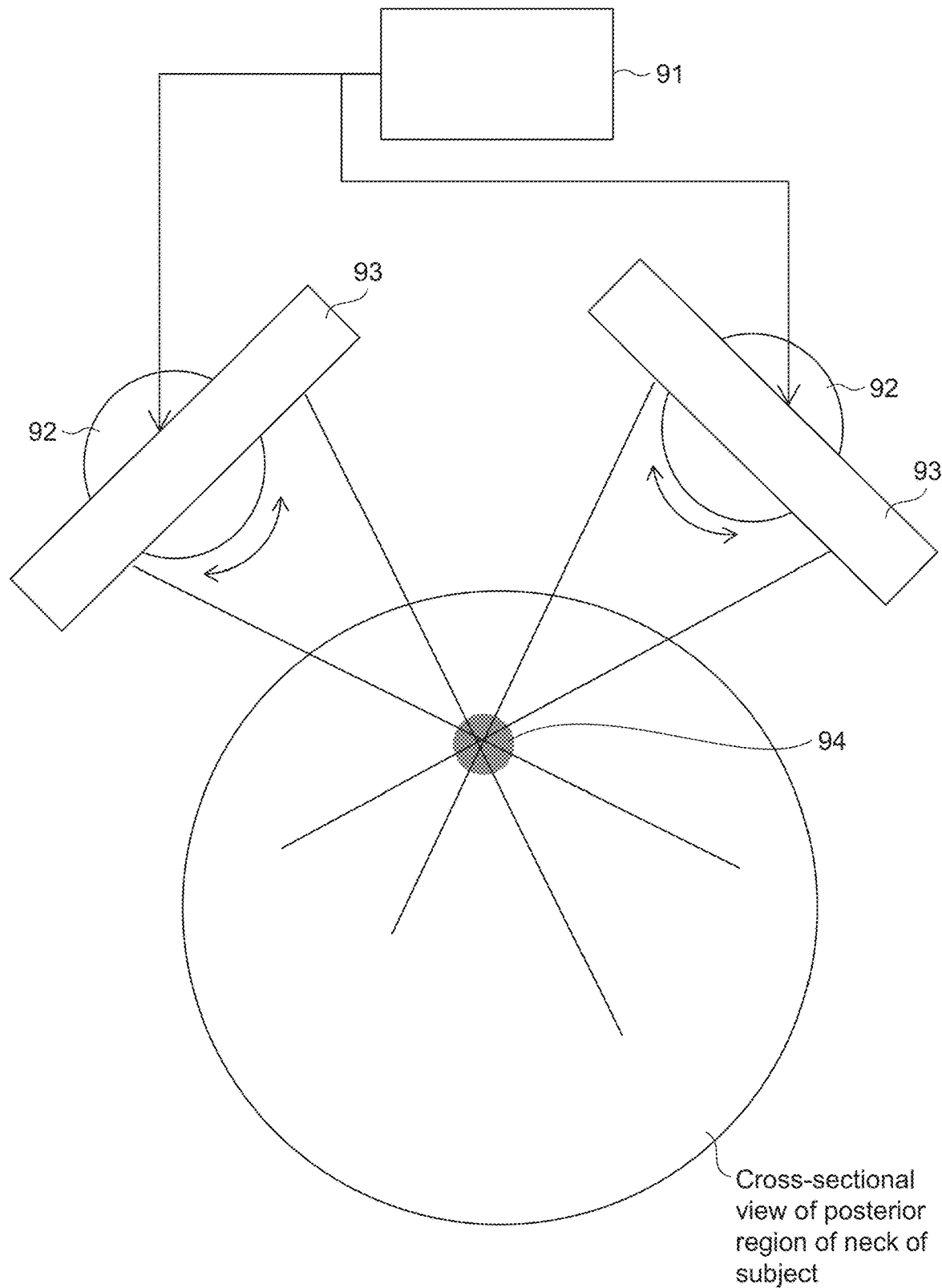
FIG. 9 shows a configuration diagram when energy emission is focused using an emission position control section of an energy emission means.

FIG. 9 shows a configuration diagram when energy emission is focused using an emission position control section of an energy emission means. To focus on a cerebrospinal fluid flow passage 94, emission position setting means 91 sets an emission position by controlling energy emission means 93 via an emission position control section 92. Since the cerebrospinal fluid flow passage 94 is not limited to one location, but is three-dimensionally distributed, temporally continuously controlling the emission position control section 92 provides an effect of preventing energy from being excessively added to a specific location and preventing a temperature at a specific location from rising excessively.

Example 6

Figure 10:
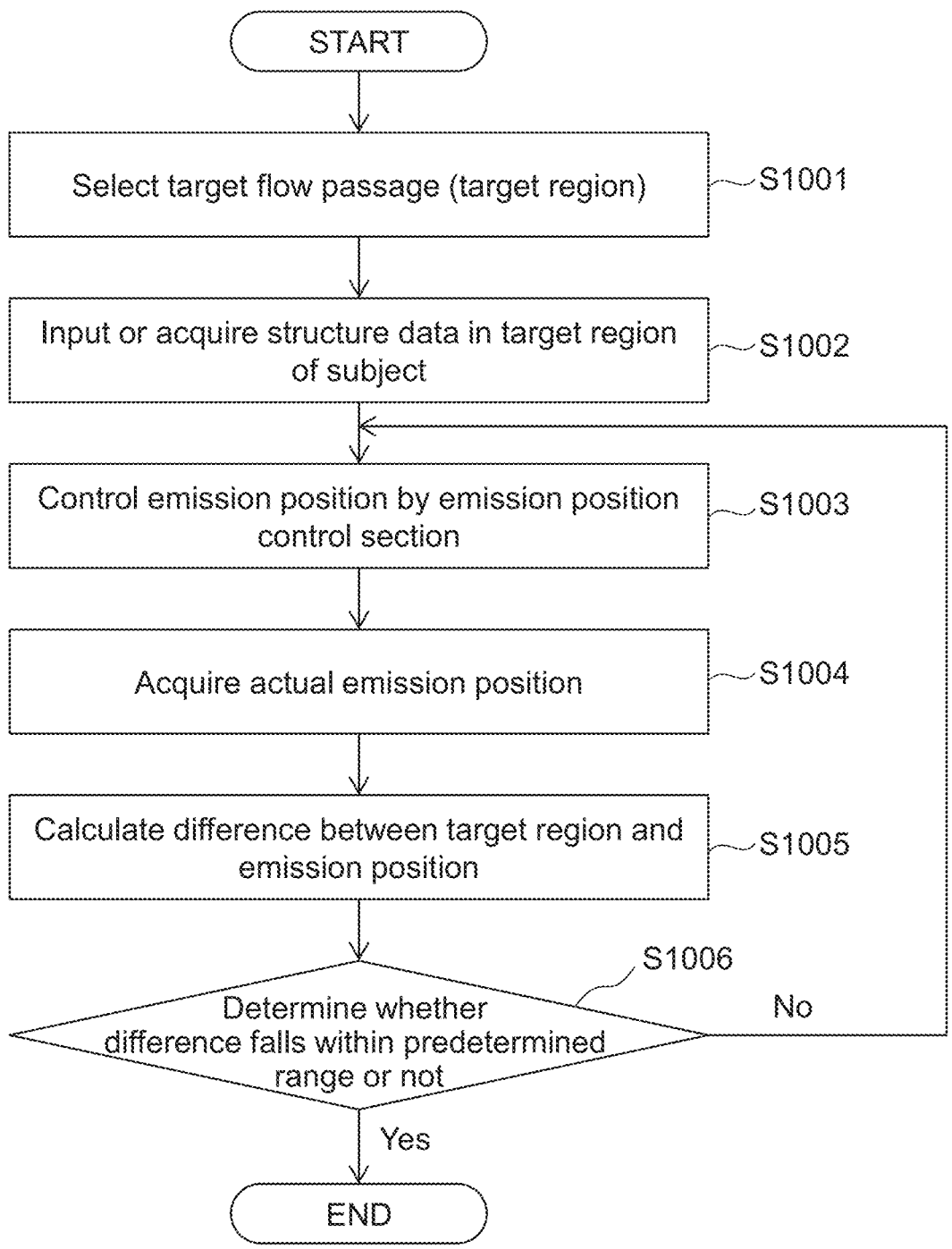
FIG. 10 is a flowchart showing how an energy emission position is set.

FIG. 10 is a flowchart showing how an energy emission position is set.

A target flow passage (target region) is selected (step S1001). Structure data in a target region of the subject is inputted or acquired (step S1002). The emission position control section controls an emission position (step S1003). An actual emission position is acquired (step S1004). A difference between the target region and the emission position is calculated (step S1005). It is determined whether the difference falls within a predetermined range or not (step S1006). When "Yes" in step S1006, the setting is ended. When "No" in step S1006, the flow moves to step S1003. This makes it possible to minimize energy consumption, minimize energy emission to the subject 10, secure safety and minimize a body temperature rise in the subject 10. That is, the present example provides an effect of not interfering with sleep.

Example 7

Figure 11:
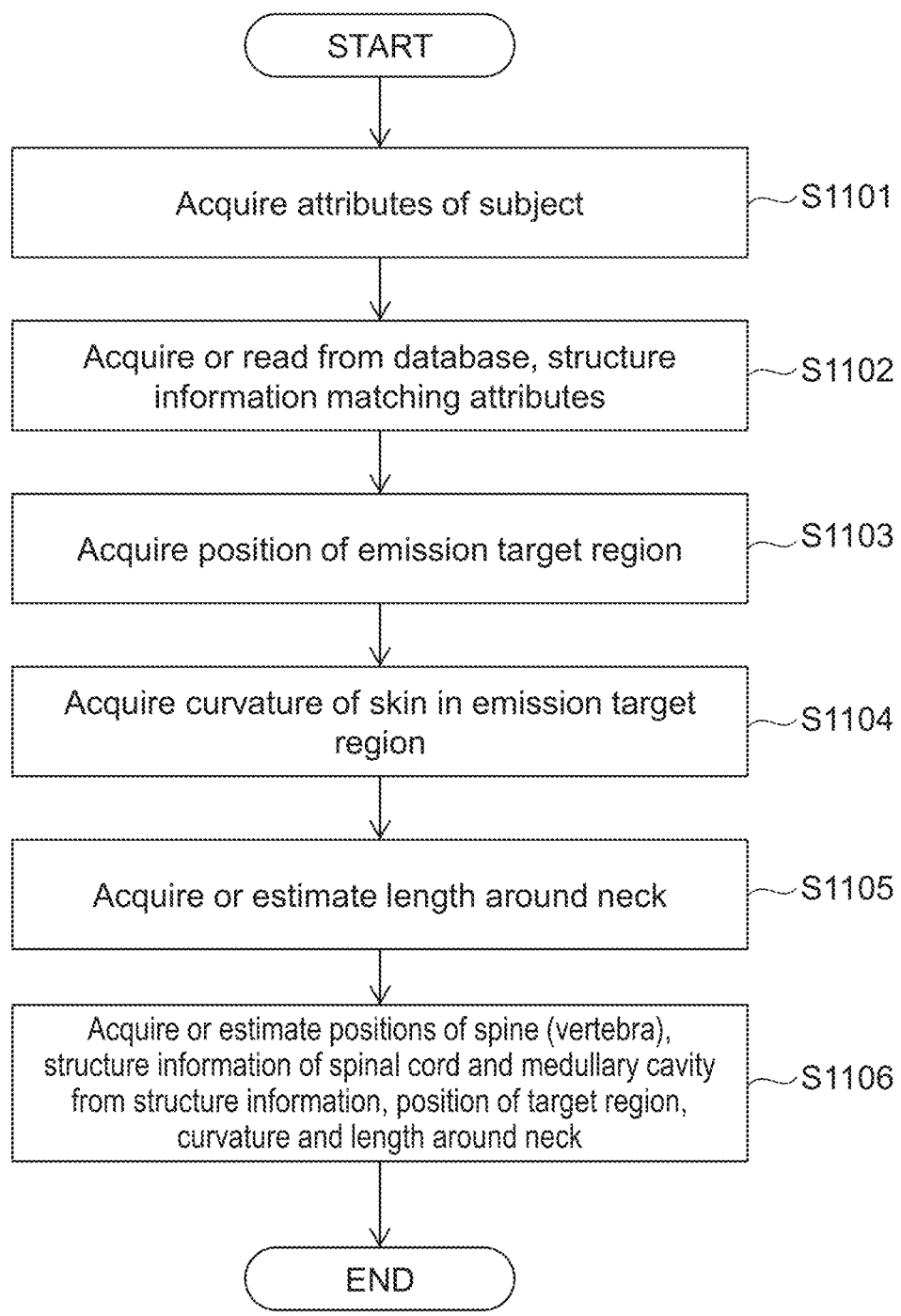
FIG. 11 is a flowchart showing how structure information such as a shape of the head or a bony framework or the spinal cord of the subject is acquired.

FIG. 11 is a flowchart showing how structure information such as a shape of the head or a bony framework or the spinal cord of the subject is acquired. Attributes of the subject 10 such as gender, age, stature and weight are acquired (step S1101). Structure information matching the attributes are acquired or read from a database (step S1102). A position of an emission target region is acquired (step S1103). In this step, a camera or an optical displacement sensor can be used. A curvature of the skin in the emission target region is acquired (step S1104). The length around the neck is acquired or estimated (step S1105). The position of the spine (vertebra) and structure information of the spinal cord and the medullary cavity are acquired or estimated from the structure information, the position of the target region, the curvature and the length around the neck (step S1106). It is thereby possible to achieve automatic and more accurate energy emission.

When performing energy emission according to such flowchart, the energy emission device may preferably further comprise a data storing means that can store standard human head structure data and head structure data, and an analysis means for deriving the positions of the cerebrospinal fluid of the subject or the flow passage thereof and/or the brain cell interstitial fluid or the flow passage thereof of the subject. Preferably, the aforementioned emission position setting means can set the emission position so that a distribution of energy emitted from a plurality of energy emission means most overlaps the position(s) of the cerebrospinal fluid or the flow passage thereof and/or the brain cell interstitial fluid or the flow passage thereof of the subject derived by the analysis means.

Example 8

Figure 12:
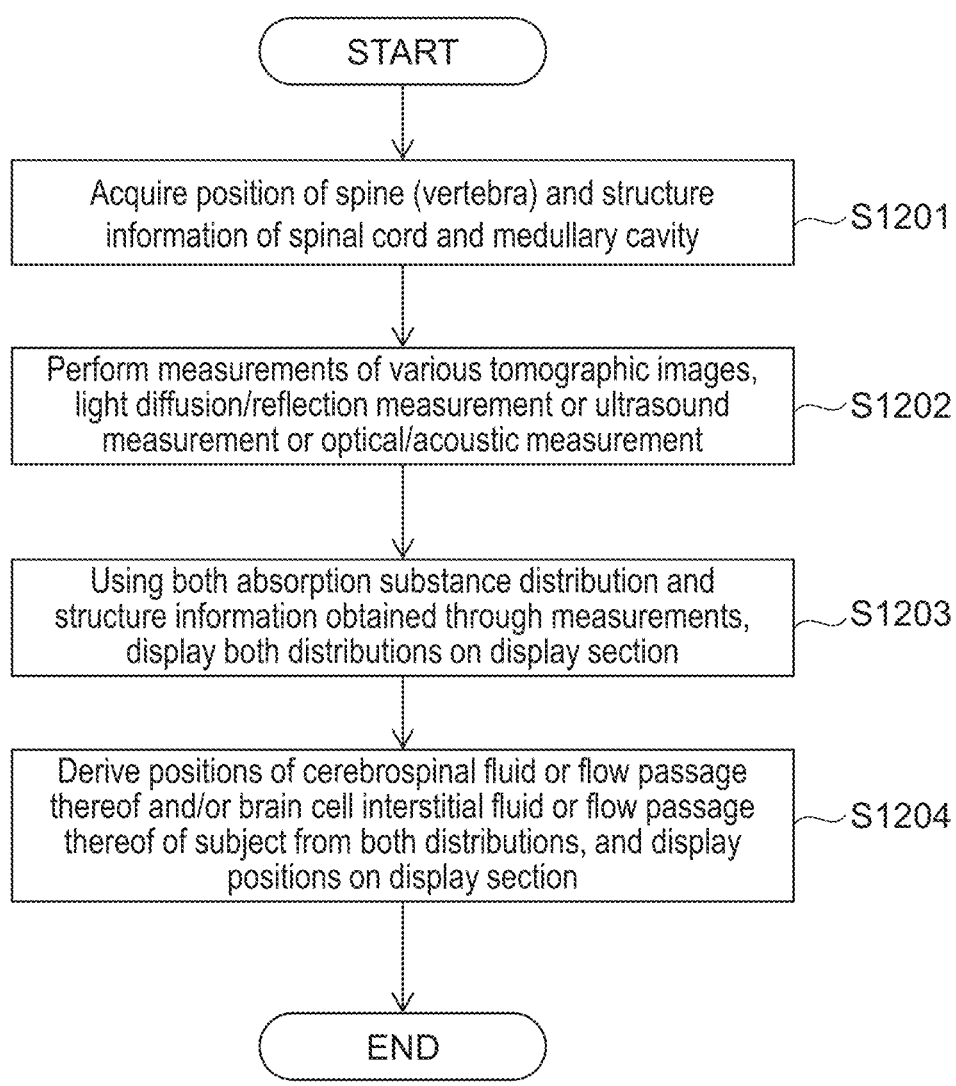
FIG. 12 is a flowchart showing how positions of the cerebrospinal fluid or the flow passage thereof and/or the brain cell interstitial fluid or the flow passage thereof of the subject are derived.

FIG. 12 is a flowchart showing how the positions of the cerebrospinal fluid or the flow passage thereof and/or the brain cell interstitial fluid or the flow passage thereof of the subject are derived. First, the position of the spine (vertebra) and structure information of the spinal cord and the medullary cavity are acquired (step S1201). Using an electromagnetic wave-receiving antenna or an ultrasound detector or photodetector, measurements of various tomographic images, light diffusion/reflection measurement or ultrasound measurement or optical acoustic measurement are performed (step S1202). The ultrasound detector may be an ultrasound transducer, a piezoelectric element or the like. The photodetector may be a photodiode, an avalanche photodiode, a photomultiplier tube or the like. Both distributions may be displayed on the display section using the absorption substance distribution and the structure information acquired from the above-mentioned measurement together (step S1203). The positions of the cerebrospinal fluid or the flow passage thereof and/or the brain cell interstitial fluid or the flow passage thereof of the subject are derived and displayed on the display section (step S1204). It is thereby possible to estimate the positions of the flow passages of the cerebrospinal fluid and the brain cell interstitial fluid in a simple manner. Displaying these positions provides an effect of visualizing effects of emission for the operator or the subject 10 and assisting the operator in determination of the emission effects.

Common to all the examples described above, it is possible to configure the device so as to monitor a concentration (amount) of predetermined substances (waste) using a means for measuring or monitoring the concentration (amount) of a predetermined substance (waste) such as Aβ concentration in the cerebrospinal fluid flow passage, to emit energy and to stop emission when a predetermined concentration (amount) is reached. The predetermined concentration here may be determined based on an average concentration of a target substance in a population of subjects having attributes equivalent to those of the subject. Information on a concentration (amount) of each of these predetermined substances may also be displayed on the display section. Furthermore, the amount of a predetermined substance in the cerebrospinal fluid flow passage may be evaluated using urine, sweat, blood or the like of the subject.

Furthermore, the device may comprise a means for estimating a CSF region from a CSF-specific image. This makes it possible to automatically determine the emission position (CSF) and aim at the emission position. The device may also be configured to comprise a movable mirror to control the emission direction. This makes it possible to adjust the emission position so that an energy distribution of emission overlaps the target (CSF distribution).

Furthermore, it is possible to calculate a position at which energy (light or the like) is distributed so as to most cover the CSF flow passage using a CSF flow passage stored in a database and emit energy to the position. For example, the device may be configured to recognize a subarachnoid cavity structure and automatically emit energy to the CSF flow. The energy emission device according to the present invention may be configured to have a temperature (body temperature, skin temperature) measuring means, a means for measuring a flow rate(s) of the cerebrospinal fluid and/or the brain cell interstitial fluid, and a means for controlling the flow rate(s) of the cerebrospinal fluid and/or the brain cell interstitial fluid to a predetermined value(s). Although the present invention assumes mainly Aβ as a discharge/control target, but not limited to Aβ, flow rates of different proteins such as α-synuclein may also be controlled.

Example 9

Figure 13:
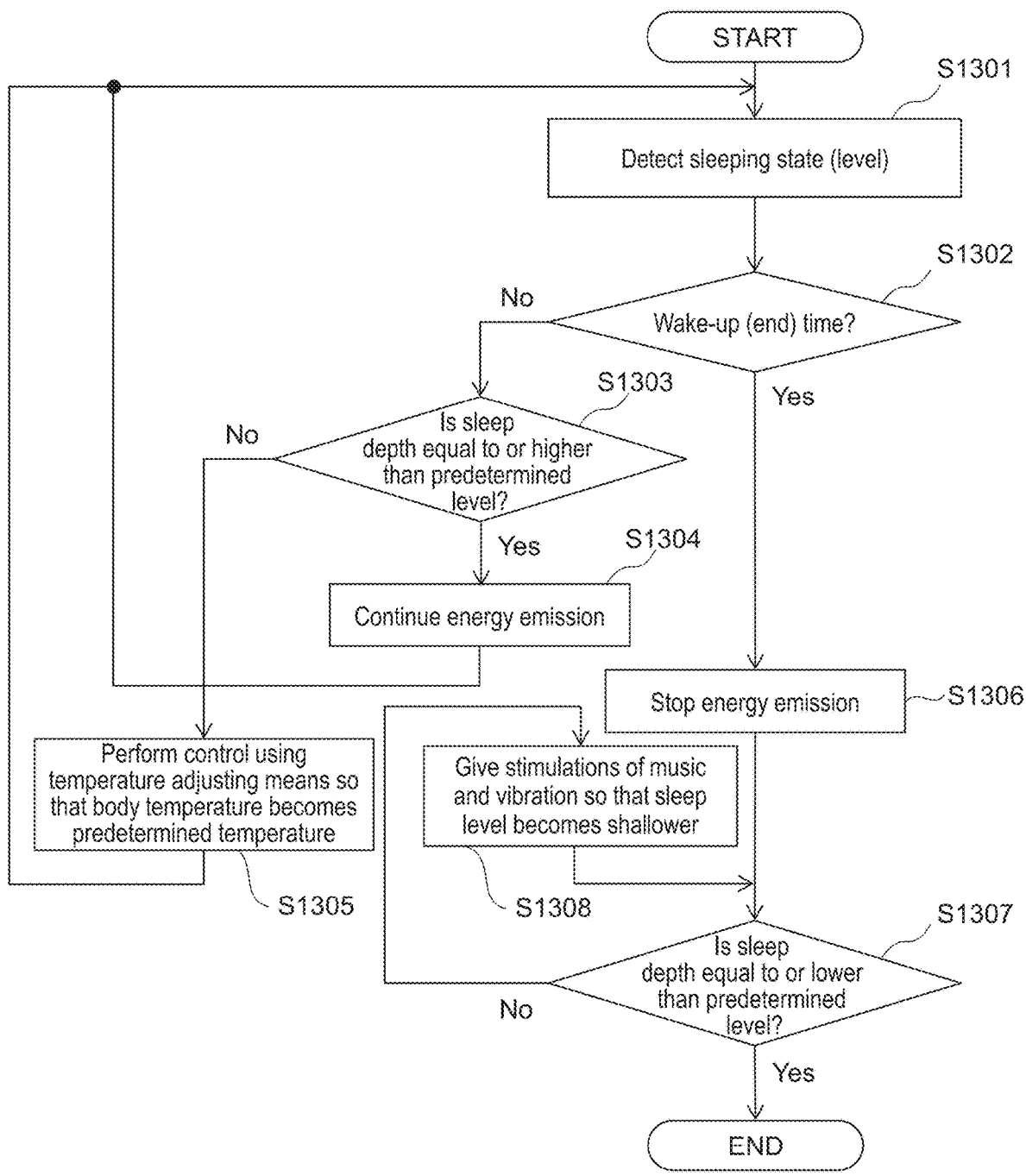
FIG. 13 is a flowchart showing how energy emission and sleep induction are controlled by monitoring wakefulness or a sleeping state of the subject.

For the purpose of reducing energy consumption (electric power, gas, and other energy resources), reducing a burden on the subject or the like, the energy emission device according to the present invention may comprise a sleep level or wakefulness controlling means so as to control the sleep level or wakefulness of the subject. FIG. 13 is a flowchart showing how energy emission and sleep induction are controlled while monitoring wakefulness or a sleeping state of the subject.

First, a sleeping state (level) is detected (step S1301). Next, it is determined whether the time corresponds to a wake-up time or emission end time (step S1302). When "No" in step S1302 (when emission is continued), it is determined whether the sleep depth is equal to or higher than a predetermined level (step S1303). For example, it may be determined whether the subject is in a non-REM sleep stage 3 or 4. When "Yes" in step S1303, energy emission is continued (step S1304) and the flow returns to step S1301. When "No" in step S1303, a temperature adjusting means performs control so that the body temperature becomes a predetermined temperature (step S1305). That is, by controlling the body temperature so as to fall within a predetermined temperature range, the sleep depth may be kept to a deep level. For example, the body temperature may be controlled to be approximately 0.5 degrees lower than that at the time of sleep onset. After that, the flow moves back to step S1301. When "Yes" in step S1302, energy emission is stopped (step S1306). It is then determined whether the sleep depth is equal to or lower than a predetermined level (step S1307). For example, it may be determined whether the sleep depth is at a REM sleep level or not. When "Yes" in step S1307, the present flow is ended. When "No" in step S1307, a stimulation presenting means gives a stimulation such as music or vibration so that the subject 10 can wake up in a shallower sleep state to ensure that the sleep level becomes shallower (step S1308). The flow then moves to step S1307 and repeatedly executes step S1308 until the sleep depth reaches or falls below a predetermined level. Such a flow using the sleep level or wakefulness controlling means allows energy emission to be performed only when the sleep depth is deep, also allows the subject to wake up when the sleep depth is shallow, thus making it possible to implement comfortable wakeup without interfering with comfortable sleep of the subject 10.

Example 10

The energy emission device according to the present invention may be further configured to detect energy to be emitted to the subject 10, measure and monitor the amount of energy. The energy detection means may be a photodiode (PD), an avalanche photodiode (APD), a photomultiplier tube or the like when energy to be emitted is light energy, or may be a piezoelectric transducer, an ultrasound resonator or the like when energy to be emitted is ultrasound and oscillatory energy, or may be an electromagnetic wave detection sensor and an antenna or the like when energy to be emitted is electromagnetic energy of an electromagnetic wave or microwave. Furthermore, the energy emission device may comprise a hemodynamics calculating means for calculating hemodynamics in a tissue in the head or other regions. Thus, measuring a variation in hemodynamics accompanying energy emission allows a variation in a cerebrovascular blood flow or a variation in a metabolic state accompanying energy emission to be monitored. This can also be used to determine validation of the amount of energy to be emitted. It is also possible to determine whether or not to continue energy emission using, for example, a variation before and after energy emission or the like from the measurement and calculation results by these energy detection means and hemodynamics calculating means.

Example 11

The energy emission device according to the present invention may use a body movement monitoring means as a reference for determining a sleep level. As the body motion monitoring means, a camera capable of taking an image of the face or body of the subject, an inertia sensor or an acceleration sensor, an angular velocity sensor, a motion sensor or the like for measuring acceleration or angular velocity of the subject. Furthermore, during energy emission, the body may preferably remain stationary for stable energy emission. In such a case, the device may be configured so as to emit energy only when body motion is of a magnitude equal to or smaller than a predetermined magnitude. It is thereby possible to improve determination accuracy of the sleep level and the sleep depth.

REFERENCE SIGNS LIST

10: Subject
11: Energy emission section
12: Sleeping state detection section
13: Energy control section
14: Cushion part
20: Optical sensor
51A to 51G: Emitter A to G
52: Skin temperature and body temperature monitor
53: Display section
54: Cerebrospinal fluid monitoring means
55: Emitter holding section
61A to 61G: Time variation in intensity of energy emitted from emitters A to G
91: Emission position setting means
92: Emission position control section
93: Energy emission means
94: Cerebrospinal fluid flow passage

The invention claimed is:

1. An energy emission device comprising:
   at least one energy emitter which emits at least one type of energy selected from the group consisting of an electromagnetic wave or an electromagnetic stimulation, an elastic wave, an oscillatory wave and heat to at least one position of a subject selected from the group consisting of the brain, the spinal cord, the cerebrospinal fluid or a flow passage thereof and the brain cell interstitial fluid or a flow passage thereof;
   a data storage which stores standard human head structure data and head structure data;
   an energy controller which controls an amount of energy emitted from the at least one energy emitter;
   a sensor which obtains information relating to wakefulness and/or a sleeping state of the subject; and
   at least one detector which detects positions of the cerebrospinal fluid or the flow passage thereof or the brain cell interstitial fluid or the flow passage thereof of the subject,
   wherein the energy controller controls the amount of energy emission depending on the information relating to the wakefulness and/or the sleeping state.

2. The energy emission device according to claim 1, wherein the at least one energy emitter is set up so as to be able to emit energy to a plurality of positions and change emission timing and/or emission intensity depending on the positions.

3. The energy emission device according to claim 1, wherein at least one emission position of energy emitted by the at least one energy emitter to at least one position selected from the group consisting of the brain, the spinal cord, the cerebrospinal fluid or the flow passage thereof and the brain cell interstitial fluid or the flow passage thereof of the subject is set.

4. The energy emission device according to claim 1, wherein structure information of a shape of the head or a bony framework or the spinal cord of the subject is acquired.

5. The energy emission device according to claim 3, wherein the said at least one emission position is set so that a distribution of energy emitted from the at least one energy emitter most overlaps a position of the cerebrospinal fluid or the flow passage thereof and/or the brain cell interstitial fluid or the flow passage thereof of the subject derived by the at least one detector.

6. The energy emission device according to claim 1, wherein the energy is detected by an energy detector and hemodynamics is calculated.

7. The energy emission device according to claim 1, further comprising a temperature measurement device configured to measure temperatures at the surface of or inside the subject.

8. The energy emission device according to claim 1, further comprising a substance measurement device which measures an amount of a predetermined substance in the cerebrospinal fluid or the flow passage thereof and/or the brain cell interstitial fluid or the flow passage thereof.

9. The energy emission device according to claim 1, further comprising a display, wherein the display displays:
   a position of the cerebrospinal fluid or the flow passage thereof and/or the brain cell interstitial fluid or the flow passage thereof derived by the at least one detector; or
   an amount of a predetermined substance in the cerebrospinal fluid or the flow passage thereof and/or the brain cell interstitial fluid or the flow passage thereof measured by a substance measurement device;
   hemodynamics calculated by a hemodynamics calculating device;
   a temperature measured by a temperature measurement device.

10. The energy emission device according to claim 1, further comprising a body motion monitor which monitors motion of the subject.

11. The energy emission device according to claim 1, wherein the sensor is at least one selected from the group consisting of a brain waves sensor, an acceleration sensor, an image sensor, an optical sensor and a heartbeat sensor.

12. The energy emission device according to claim 1, further comprising a controller which controls a sleep level or wakefulness of the subject.

13. An energy emission device comprising:
   at least one energy emitter which emits at least one type of energy selected from the group consisting of an electromagnetic wave or an electromagnetic stimulation, an elastic wave, an oscillatory wave and heat to at least one position of a subject selected from the group consisting of the brain, the spinal cord, the cerebrospinal fluid or a flow passage thereof and the brain cell interstitial fluid or a flow passage thereof;
   an energy controller which controls an amount of energy emitted from the at least one energy emitter; and
   a sensor which obtains information relating to wakefulness and/or a sleeping state of the subject; and
   a flow rate measurement device which measures a flow rate of the cerebrospinal fluid and/or the brain cell interstitial fluid of the subject,
   wherein the energy controller controls the amount of energy emission depending on the information relating to the wakefulness and/or the sleeping state.

14. The energy emission device according to claim 13, further comprising a flow rate controller which controls a flow rate of the cerebrospinal fluid and/or the brain cell interstitial fluid of the subject so as to have predetermined values.

15. An energy emission device comprising:
- at least one energy emitter which emits at least one type of energy selected from the group consisting of an electromagnetic wave or an electromagnetic stimulation, an elastic wave, an oscillatory wave and heat to at least one position of a subject selected from the group consisting of the brain, the spinal cord, the cerebrospinal fluid or a flow passage thereof and the brain cell interstitial fluid or a flow passage thereof;
- at least one detector which detects positions of the cerebrospinal fluid or the flow passage thereof and/or the brain cell interstitial fluid or the flow passage thereof of the subject;
- an energy controller which controls an amount of energy emitted from the at least one energy emitter; and
- a sensor which obtains information relating to wakefulness and/or a sleeping state of the subject,
- wherein the energy controller controls the amount of energy emission depending on the information relating to the wakefulness and/or the sleeping state.

16. The energy emission device according to claim 15, wherein at least one emission position of energy emitted by the at least one energy emitter to at least one position selected from the group consisting of the brain, the spinal cord, the cerebrospinal fluid or the flow passage thereof and the brain cell interstitial fluid or the flow passage thereof of the subject is set.

17. The energy emission device according to claim 16, wherein the at least one emission position is set so that a distribution of energy emitted from the at least one energy emitter most overlaps a position of the cerebrospinal fluid or the flow passage thereof and/or the brain cell interstitial fluid or the flow passage thereof of the subject derived by the at least one detector.

18. The energy emission device according to claim 15, said at least one emission position of energy is emitted by the at least one energy emitter to at least one position selected from the group consisting of the brain, the spinal cord, the cerebrospinal fluid or the flow passage thereof and the brain cell interstitial fluid or the flow passage thereof of the subject is set.

19. The energy emission device according to claim 18, wherein the at least one emission position is set so that a distribution of energy emitted from the at least one energy emitter most overlaps the position of the cerebrospinal fluid or the flow passage thereof and/or the brain cell interstitial fluid or the flow passage thereof of the subject derived by the at least one detector.

* * * * *